US008183286B2

(12) United States Patent
Faulds et al.

(10) Patent No.: US 8,183,286 B2
(45) Date of Patent: May 22, 2012

(54) EP2 AND EP4 AGONISTS AS AGENTS FOR THE TREATMENT OF INFLUENZA A VIRAL INFECTION

(75) Inventors: Daryl Faulds, Mill Valley, CA (US);
William J. Guilford, Belmont, CA (US);
Wolfgang Seifert, Berlin (DE)

(73) Assignee: Gemmus Pharma Inc., San Francisco, CA (US)

( * ) Notice: Subject to any disclaimer, the term of this patent is extended or adjusted under 35 U.S.C. 154(b) by 448 days.

(21) Appl. No.: 11/985,335

(22) Filed: Nov. 14, 2007

(65) Prior Publication Data
US 2009/0170931 A1 Jul. 2, 2009

Related U.S. Application Data

(60) Provisional application No. 60/859,590, filed on Nov. 16, 2006.

(51) Int. Cl.
*A61K 31/34* (2006.01)
(52) U.S. Cl. .................... 514/470; 514/473
(58) Field of Classification Search .................. 514/470
See application file for complete search history.

(56) References Cited

U.S. PATENT DOCUMENTS

| | | | |
|---|---|---|---|
| 4,219,479 A | 8/1980 | Vorbrueggen et al. |
| 4,423,067 A | 12/1983 | Skuballa et al. |
| 4,474,802 A | 10/1984 | Ohno et al. |
| 4,692,464 A | 9/1987 | Skuballa et al. |
| 4,708,963 A | 11/1987 | Skuballa et al. |
| 5,010,065 A | 4/1991 | Skuballa et al. |
| 5,013,758 A | 5/1991 | Skuballa et al. |
| 5,049,582 A | 9/1991 | Adler et al. |
| 5,663,203 A | 9/1997 | Ekerdt et al. |
| 6,235,780 B1 | 5/2001 | Ohuchida et al. |
| 6,410,591 B1 | 6/2002 | Burk et al. |
| 6,747,037 B1 | 6/2004 | Old et al. |
| 2003/0166631 A1 | 9/2003 | Dumont et al. |
| 2005/0080140 A1 | 4/2005 | Hatae et al. |
| 2007/0197524 A1 | 8/2007 | Brauer et al. |

FOREIGN PATENT DOCUMENTS

| | | |
|---|---|---|
| DE | 10 2005 062741 (A1) | 6/2007 |
| EP | 0860430 A2 | 8/1998 |
| EP | 0974580 A1 | 1/2000 |
| EP | 1563846 A1 | 8/2005 |
| WO | WO 0020371 A1 * | 4/2000 |
| WO | WO 2004/012656 A2 | 2/2004 |
| WO | WO 2004/012656 A3 | 2/2004 |
| WO | WO 2007/057232 A1 | 5/2007 |
| WO | WO 2007/101111 A2 | 9/2007 |
| WO | WO 2007/101111 A3 | 9/2007 |
| WO | WO2008/058766 A1 | 5/2008 |

OTHER PUBLICATIONS

Chan et al. Proinflammatory cytokine responses induced by influenza A (H5N1) viruses in primary human alveolar and bronchial epothelial cells, Respiratory Research, 2005, vol. 6:135 http://respiratory-research.com/content/6/1/135.*
Trudeau et al. "Selective downregulation of prostaglandin E2-related pathways by the TH2 cytokine IL-13," J. Allergy Clin. Immunnol. May 2006, vol. 117, No. 6., pp. 1446-1454.*
Augustin, S L et al: Perfusion, 2006, pp. 121-125, vol. 21, No. 2, Edward Arnold (Publishers) Ltd.
Rainsford, K D: Inflammopharmacology, 2006, pp. 2-9, vol. 14, No. 1-2, Birkhaeuser Verlag, Basel.
Clarke, D L et al:British Journal of Pharmacology, 2004, pp. 1141-1150, vol. 141, No. 7, Nature Publishing Group, UK.
Tanaka, Hiroshi et al: Chest, 2005, pp. 3717-3723, vol. 128, No. 5, American College of Chest Physicians, US.
de Jong MD, Simmons CP, Thanh TT, Hien VM, Smith GJ, Chau TN, Hoang DM, Chau NV, Khanh TH, Dong VC, Qui PT, Cam BV, Ha do Q, Guan Y, Peiris JS, Chinh NT, Hien TT, Farrar J (2006) Fatal outcome of human influenza A (H5N1) is associated with high viral load and hypercytokinemia. *Nat. Med.* 12(10):1203-1207.
Heltzer ML, Coffin SE, Maurer K, Bagashev A, Zhang Z, Orange JS, Sullivan KE, Immune dysregulation in severe influenza, J Leukocyte Biol 2009;85:1036-1043.
Mok KP, Wong CHK, Cheung CY, Chan MC, Lee SMY, Nicholls JM, Guan Y, Peiris JSM, Viral Genetic Determinants of H5N1 Influenza Viruses That Contribute to Cytokine Dysregulation, J Infect Dis 2009; 200:000-000.
Cinatl J, Michaelis M, Doerr HW. The threat of avian influenza a (H5N1): part II: Clues to pathogenicity and pathology Med Microbiol Immunol 2007; 196:191-201.
Fedson DS Confronting the next influenza pandemic with anti-inflammatory and immunomodulatory agents: why they are needed and how they might work Influenza and Other Respiratory Viruses 2009;3, 129-142.
Neveu WA, Allard JL, Raymond DM, Bourassa LM, Burns SM, Bunn JY, Irvin CG, Kaminsky DA, Rincon M, Elevation of IL-6 in the allergic asthmatic airway is independent of inflammation but associates with loss of central airway function, Respir Res 2010; 11:28.
Wills-Karp M, Luyimbazi J, Xu X, Schopield B, Neben TY, Karp CL, Donaldson DD, Interleukin-13: Central Mediator of Allergic Asthma, Science1998; 282:2258.
Gruenig G, Warnock M, Wakil AE, Venkayya R, Brombacher F, Rennick DM, Sheppard D, Mohrs M, Donaldson DD, Locksley RM, Corry DB Requirement for IL-13 Independently of IL-4 in Experimental Asthma Science1998; 282:2261.
Fadel SA, Bromley SK, Medoff BD, Luster AD, CXCR3-deficiency protects influenza-infected CCR5-deficient mice from mortality Eur. J. Immunol. 2008. 38: 3376-3387.
Beck MA, Nelson HK, Shi Q , Van Dael P, Schiffrin EJ, Blum S , Barclay D, Levander OA, Selenium deficiency increases the pathology of an influenza virus infection, FASEB J, 2001;15:1481-1483.
Butler D (2007) Cheaper approaches to flu divide researchers. *Nature* 448(30): 976-977.

(Continued)

Primary Examiner — Shengjun Wang
(74) Attorney, Agent, or Firm — Weaver Austin Villeneuve & Sampson LLP; Tom Hunter

(57) ABSTRACT

The present invention is directed to the use of EP2 and/or EP4 agonists as therapeutics for the treatment of diseases associated with influenza A viruses, such as for example H5N1 and mutations thereof.

18 Claims, No Drawings

OTHER PUBLICATIONS

Salomon R, Hoffmann E, Webster RG (2007) Inhibition of the cytokine response does not protect against lethal H5N1 influenza infection *Prod. Natl. Acad. Sci. USA*.104(30):12479-12481.

Szretter KJ, Gangappa S, Lu X, Smith C, Shieh WJ, Zaki SR, Sambhara S, Tumpey TM, Katz JM (2007) Role of host cytokine responses in the pathogenesis of avian H5N1 influenza viruses in mice. *J. Virol.* 81(6):2736-44.

Kobayashi T, Narumiya S, Function of prostanoid receptors: studies on knockout mice Prostaglandin Other Lipid Mediat 2002;68-69:557-73.

Honda T, Segi-Nishida E, Miyachi Y, Narumiya S. Prostacyclin-IP signaling and prostaglandin E2-EP2/EP4 signaling both mediate joint inflammation in mouse collagen-induced arthritis. J Exp Med. Feb. 20, 2006;203(2):325-35.

Yao C, Sakata D, Esaki Y, Li Y, Matsuoka T, Kuroiwa K, Sugimoto Y, Narumiya S. Prostaglandin E2-EP4 signaling promotes immune inflammation through Th1 cell differentiation and Th17 cell expansion. Nat Med. Jun. 2009;15(6):633-40.

Hristovska AM, Rasmussen LE, Hansen PB, Nielsen SS, Nüsing RM, Narumiya S, Vanhoutte P, Skøtt O, Jensen BL, Prostaglandin E2 induces vascular relaxation by E-prostanoid 4 receptor-mediated activation of endothelial nitric oxide synthase. Hypertension. 2007;50(3):525-30.

Gilroy DW, et al. Inducible cyclooxygenase may have anti-inflammatory properties. Nat Med 1999;5:698-701.

Sugimoto Y, Narumiya S. Prostaglandin E receptors. J Biol Chem. 2007;282(16):11613-7.

Matsuoka T, Narumiya S. Prostaglandin receptor signaling in disease. ScientificWorldJournal. 2007;7:1329-47.

Written Opinion of the International Searching Authority for PCT/EP2007/009996 filed Nov. 14, 2007.

EPO Communication pursuant to Article 94(3) EPC dated Nov. 2, 2010.

Response to EPO Communication dated Nov. 2, 2010 dated Jul. 28, 2010.

Hien, et al., "Avian Influenza a (H5N1) in 10 Patients in Vietnam", The New England Journal of Medicine, vol. 350 No. 12, Mar. 18, 2004, 1179-1188 (10 pgs).

Chotpitayasunondh, et al., "Human Disease from Influenza A (H5N1), Thailand, 2004", Emerging Infectious Diseases, www.cdc.gov/eid, vol. 11, No. 2, Feb. 2005, 201-209 (9 pgs).

Jacoby, et al., "Influenza infection causes airway hyperresponsiveness by decreasing enkephalinase", Journal of Applied Physiology, Jun. 1, 1988, 64:2653-2658 (6 pgs).

Wills-Karp, et al., "Interleuken-13: Central Mediator of Allergic Asthma", Science, www.sciencemag.org, Dec. 18, 1998, vol. 282, 2258-2261 (4 pgs).

Hatae, et al., "Prostacyclin-dependent Apoptosis Mediated by PPAR", The Journal of Biological Chemistry, vol. 276, No. 49, Issue of Dec. 7, pp. 46260-46267, 2001 (8 pgs.).

MCW Chan, et al., "Proinflammatory Cytokine responses Induced by Influenza A(H5N1) Viruses in Primary Human Alveolar And Bronchial Epithelial Cells", http: //respiratory-research.com/content/6/1/135, *Respiratory Research* 2005, 6:135 (13 pgs.).

John Trudeau, BA, et al., "Selective downregulation of prostaglandin E2—related pathways by the TH2 cytokine IL-13", J Allergy Clin Immunol vol. 117, No. 6, Jun. 2006 (9 pgs.).

John P. Buchweitz, et al., "Time-Dependent Airway Epithelial and Inflammatory Cell Responses Induced by Influenza Virus A/PR/8/34 in C57BL/6 Mice", *Toxicologic Pathology*, 35:424-435, 2007 (13 pgs.).

Bo-Jian Zheng, et al., "Delayed Antiviral Plus Immunomodulator Treatment Still Reduces Mortality in Mice Infected by High Inoculum of Influenza A/H5N1 Virus", PNAS Jun. 10, 2008 vol. 105 No. 23 8091-8096 (6 pgs.).

Meredith Vandermeer, MPH, et al., "Role of Statins in Preventing Death Among Patients Hospitalized with Lab-confirmed Influenza Infections", IDSA 2009, (1 pg.).

Jesus F Bermejo-Martin, et al., "Th1 and Th17 Hypercytokinemia as Early Host Response Signature in Severe Pandemic Influenza", Critical Care vol. 13 No. 6, http://ccforum.com/content/13/6/R201, (11 pgs.), 2009.

U.S. Appl. No. 13/073,889, filed Mar. 28, 2011, Faulds et al.

PCT International Search Report dated Mar. 17, 2008 issued in PCT/EP2007/009996.

PCT International Preliminary Report on Patentability and Written Opinion dated May 19, 2009 issued in PCT/EP2007/009996.

EP Communication pursuant to Article 94(3) EPC dated Oct. 8, 2010 issued in EP 07 846 671.1-1216.

Response to EPO Communication dated Oct. 8, 2010 dated Nov. 3, 2010 in EP 07 846 671.1-1216.

EP Extended European Search Report dated Feb. 10, 2012 issued in EP 10 186 781.0-1216.

* cited by examiner though pictured as a single diastereomer, both the α and β anomers are within the scope of the present invention.

EP2 AND EP4 AGONISTS AS AGENTS FOR THE TREATMENT OF INFLUENZA A VIRAL INFECTION

This application claims the benefit of and priority to U.S. Ser. No. 60/859,590, filed on Nov. 16, 2006, which application is hereby incorporated by reference in its entirety.

FIELD OF THE INVENTION

The present invention is directed to the use of EP2 and/or EP4 agonists as therapeutics for the treatment of human respiratory diseases associated with influenza A viruses, such as for example H5N1 and its mutations.

BACKGROUND OF THE INVENTION

The effects of prostaglandins are mediated by their G protein-coupled receptors which are located on the cell surface. Prostaglandin $E_2$ ($PGE_2$) is of particular interest, having a wide variety of cellular effects through binding to functionally different receptor subtypes, namely the EP1, EP2, EP3 and EP4 receptors, all of which respond to $PGE_2$ but differ in their actions.

Dendritic cells (DC) are the most potent antigen-presenting cells of the immune system. Cytokine production by mature antigen-carrying DC within lymph nodes is strongly influenced by $PGE_2$ during their activation in peripheral tissues. Inflammatory cytokines such as IL-1β and TNF-α activate antigen-carrying DC to secrete IL-12 and promote the development of T-helper type 1 (Th-1) cytokine expression-biased cells. In contrast, DC activated in the presence of $PGE_2$ show impaired IL-12 production and promote the development of T-helper type 2 (Th-2) cytokine expression-biased cells [Hilkens C M et al., *J. Immunol.* 156:1722-27 (1996)]. The difference in the ability to produce IL-12 in response to $PGE_2$, established during DC activation in the peripheral tissues, is stable to the removal of cytokines and $PGE_2$.

Increased production of cytokines triggers inflammation, a normal response by the body to help fight a virus. However, when cytokine production becomes prolonged or excessive it can inflame airways, making it hard to breathe, which in turn can result in pneumonia and acute respiratory distress; and it can injure other organs, which can result in severe life-threatening complications.

It has recently been demonstrated that influenza A subtype H5N1 viruses associated with the recent outbreaks of avian flu in Asia are more potent inducers of inflammatory cytokines and chemokines in primary human alveolar and bronchial epithelial cells in vitro in comparison to the more common, less virulent human flu virus H1N1. Levels of cytokines and chemokines were from 3 times to more than 10 times higher in the human cells infected with the H5N1 virus than those infected with H1N1 (N C W Chan, et al. *Respiratory Research* 2005, 6:135; article URL: http://respiratory-research.com/content/6/1/135).

These test data correlate with the high levels of cytokines and chemokines seen in patients afflicted with the avian flu, indicating that the hyper-induction of cytokines and/or chemokines is likely relevant to the pathogenesis of human H5N1 disease. Standard steroid anti-inflammatory therapy against avian flu has been of little therapeutic value. Tamiflu has shown efficacy in that mice infected with H5N1 influenza virus survived when treated. For cases of human infection with H5N1, Tamiflu may improve prospects for survival but clinical data are limited. Concerns have been recently raised about the safety of Tamiflu treatment to patients having the avian flu.

It would therefore be desirable to have a therapeutic agent that inhibits the release of overstimulated cytokines and chemokines, especially TNFα interferon gamma (IFN-γ) and Interferon gamma. It would also be desirable to have a therapeutic agent that would treat diseases associated with human H5N1 and other influenza A subtype viruses while being well-tolerated by the patients.

European patent EP 1306087 describes EP2 receptor agonists which are used in the treatment of erectile dysfunction. The same structural class is described in European patent EP 860430, and their use for producing a medicament for the treatment of immunological disorders, asthma and abortion is claimed. PCT publication WO 04/32965 describes EP2 receptor agonists which are used for the treatment and prevention of disorders caused by an organ dysfunction caused by ischemia. WO 04/009117 describes EP2 and EP4 receptor agonists for the treatment of disorders caused by uterine contraction, for example painful menstruation. WO 03/074483 and WO 03/009872 describe agonists which bind equally to the EP2 and the EP4 receptor (Ono Pharmaceuticals). Agonists of the EP2 and of the EP4 receptor are frequently described in connection with the treatment of osteoporosis (WO 99/19300, US 2003/0166631, WO 03/77910, WO 03/45371, WO 03/74483 and WO 03/09872) and for glaucoma treatment (WO 04/37813, WO 04/37786, WO 04/19938, WO 03/103772, WO 03/103664, U.S. Pat. No. 6,747,037, U.S. Pat. No. 6,410,591, WO 03/40123, WO 03/47513, WO 03/47417). WO 04/12656 claims EP2 receptor agonists in connection with inflammation. WO 03/77919 claims EP4 receptor agonists for the treatment of fertility.

SUMMARY OF THE INVENTION

The present invention is directed to agents that are useful as therapeutics against viral diseases. More particularly, the invention is directed to a method of treating diseases associated with influenza A virus, and especially with the influenza A subtype H5N1 virus. The method comprises administering to a patient in need thereof an effective amount of an EP2 agonist, an EP4 agonist, a mixed EP2/EP4 agonist, or mixtures thereof (all of which are encompassed herein under the terms "EP2 and EP4 agonists", "EP2 and/or EP4 agonists", and "EP agonists").

DETAILED DESCRIPTION OF THE INVENTION

EP2, EP4, and mixed EP2/EP4 agonists useful in the present invention include all those that inhibit the release of cytokines and/or chemokines in response to infection by influenza A viruses and, in a preferably preferred embodiment, by the influenza A subtype H5N1 virus. Such inhibition can be determined by one of skill in the art by methods known in the art or as taught herein, without undue experimentation.

In one presently preferred embodiment, the agonists are selected from 5-cyanoprostacyclin derivatives. 5-Cyanoprostacyclin derivatives and certain of their pharmacological effects are known from U.S. Pat. Nos. 4,219,479 and 5,049,582, the entire disclosures of which are incorporated herein by reference. It is believed that these compounds exhibit both EP2 and EP4 agonistic activity (a mixed EP2/EP4 agonist). The production of these compounds and the pharmaceutically acceptable salts thereof are described in detail in the above US patents. Cyclodextrin clathrates of the 5-cyano-prostacyclin derivatives are also included within the scope of the present invention; they are disclosed and claimed in U.S. Pat. No. 5,010,065, the entire disclosure of which is incorporated herein by reference. The above 5-cyanoprostacyclin derivatives have not been previously disclosed as being effective in the treatment or prevention of viral diseases, and this new pharmacological property also has no direct connection with the effects described in the US patents.

In a presently preferred embodiment, the 5-cyanoprostacyclin derivative useful in treating viral diseases according to the present invention is Nileprost, 5-cyano-15-methylprostacyclin:

Nileprost

[structure: Nileprost]

It has now been found that the above-described 5-cyano-prostacyclin derivatives inhibit the release of Th-1 cytokines while sparing the expression of Th-2 cytokines and enhance a polarization of T cells recruitment towards the Th-2 response and away from the Th-1 response. This makes them desirable as pharmaceuticals for treating diseases associated with viruses and particularly with the influenza A H5N1 subtype. This is particularly true since they are distinguished over natural prostaglandins by an improved specificity, longer period of effectiveness and higher stability. Additionally, these compounds have been found in clinical phase I studies to be well-tolerated by humans and to have no hypotensive effects, making them further suitable as pharmaceuticals and anti-flu therapeutics.

In a second presently preferred embodiment of the invention, the EP2 agonist is selected from certain prostacyclin and carbacyclin derivatives that are disclosed, together with methods for their synthesis, in, e.g., U.S. Pat. Nos. 4,423,067, 4,474,802, 4,692,464, 4,708,963, 5,013,758 and/or CA 1248525, the entire disclosures of which are incorporated herein by reference. These prostacyclin and carbacyclin derivatives have not been previously disclosed as being effective in the treatment or prevention of viral diseases, and this new pharmacological property also has no direct connection with the effects described in the US patents.

In a presently preferred embodiment, the prostacyclin or carbacyclin derivative useful in treating viral diseases according to the present invention is selected from Iloprost, Cicaprost, Eptaloprost, Beraprost, and Ciprosten. In a more preferred embodiment, the prostacyclin analog is Beraprost, (+/−)-(1R*,2R*,3as*,8bS*)-2,3,3a,8b-tetrahydro-2-hydroxy-1-[(E)-(3S*)-3-hydroxy-4-methyl-1-octen-6-ynyl]-1H-cyclopenta[b]benzofuran-5-butyrate:

[structure: Beraprost]

In yet another embodiment of the invention, the EP2 agonist is selected from the 9-chloro-15-deoxyprostaglandin derivatives of the general formula I:

[structure of Formula I]

wherein
$R^1$ is a $CH_2OH$, a —$COOR^2$, a —$CONHR^2$ or a —$CONHR^3$ group,
$R^2$ is a hydrogen,
a $C_1$-$C_{10}$-alkyl radical which is linear or branched, optionally mono- to polyunsaturated and is optionally mono- to poly-substituted by halogen, $C_1$-$C_4$-alkoxy, substituted $C_3$-$C_{10}$-aryl, optionally substituted $C_3$-$C_{10}$-aroyl, optionally substituted di-$C_1$-$C_5$-alkylamino or optionally substituted tri-$C_1$-$C_5$-alkylamino,
a $C_3$-$C_{10}$-cycloalkyl which is optionally substituted by $C_1$-$C_4$-alkyl,
a $C_3$-$C_{10}$-aryl which is optionally substituted by phenyl, 1-naphthyl, 2-naphthyl which in turn may be substituted in position 3 and in position 4 by fluorine, chlorine, alkoxy or trifluoromethyl or in position 4 by hydroxy, halogen, phenyl, one or more $C_1$-$C_4$-alkyl groups, chloromethyl, fluoromethyl, trifluoromethyl, carboxy, hydroxy or $C_1$-$C_4$-alkoxy,
or a $C_3$-$C_7$-heterocycloalkyl,
$R^3$ is a $C_1$-$C_{15}$-carboxylic acid or a $C_1$-$C_{15}$-sulphonic acid,
A is a cis-CH═CH— or —$CH_2$—$CH_2$— group,
B is a trans-CH═CH— or —$CH_2$—$CH_2$— group,
W is a $C_2$-$C_6$-alkylene,
$R^4$ is a hydroxy group, a radical O—$R^6$ or O—$R^7$, where $R^6$ is a tetrahydropyranyl, tetrahydrofuranyl, trimethylsilyl, tert-butyldimethylsilyl, tert-butyldiphenylsilyl or tribenzylsilyl radical and $R^7$ is a $C_1$-$C_{15}$-carboxylic acid,
$R^5$ is a hydrogen, a $C_1$-$C_{10}$-alkyl or a $C_1$-$C_{10}$-alkenyl group,
n is the number 1-4,
and the salts thereof and the cyclodextrin clathrates thereof with physiologically tolerated bases.

Alkyl groups are linear or branched alkyl groups, saturated and unsaturated alkyl radicals having 1-10 C atoms. Examples which may be mentioned are methyl, ethyl, propyl, butyl, isobutyl, tert-butyl, pentyl, neopentyl, hexyl, heptyl, octyl, decyl, butenyl, isobutenyl, propenyl, pentenyl, benzyl, m- and p-chlorobenzyl groups. The alkyl groups may optionally be mono- to polysubstituted by halogen atoms (e.g. fluorine, chlorine or bromine), by alkoxy groups (such as, for example, methoxy, ethoxy or propoxy), by substituted aryl or aroyl groups (e.g. phenyl), or by dialkylamino (e.g. dimethylamino, diethylamino, dimethylaminopropyl or trialkylammonium), where monosubstitution is to be preferred.

Suitable aryl groups are both substituted and unsubstituted aryl groups such as, but not limited to, phenyl, 1-naphthyl and 2-naphthyl. Substituents may be selected from, for example, 1 to 3 halogen atoms, a phenyl group, 1 to 3 alkyl groups each having 1-4 carbon atoms, chloromethyl, fluoromethyl, trifluoromethyl, carboxy, hydroxyl, or an alkoxy group having 1-4 carbon atoms.

The cycloalkyl group comprises 3-10 carbon atoms in the ring. The ring may be substituted by alkyl groups having 1-4 carbon atoms. Examples of cycloalkyl groups include, but are not limited to, cyclopentyl, cyclohexyl, methylcyclohexyl and adamantyl.

Suitable heterocyclic groups are 5- and 6-membered heterocycles which comprise at least 1 heteroatom, preferably nitrogen, oxygen or sulphur. Examples include, but are not limited to, 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, and 2-tetrazolyl.

Physiologically tolerated acid residues are suitable as acid residue. Preferred acids are organic carboxylic acids and sulphonic acids having 1-15 carbon atoms which belong to the aliphatic, cycloaliphatic, aromatic, and heterocyclic series. Examples which may be mentioned of substituents are $C_1$-$C_{15}$-alkyl, hydroxy, $C_1$-$C_{15}$-alkoxy, oxo groups, amino groups and halogen atoms. Examples of carboxylic acids which may be mentioned are formic acid, acetic acid, propionic acid, butyric acid, isobutyric acid, valeric acid, isovaleric acid, caproic acid, oenanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy or carboxy groups, nicotinic acid, isonicotinic acid, furan-2-carboxylic acid, and cyclopentylpropionic acid. Examples of suitable sulphonic acids are methanesulphonic acid, ethanesulphonic acid, isopropanesulphonic acid, β-chloroethanesulphonic acid, butanesulphonic acid, cyclopentanesulphonic acid, cyclohexanesulphonic acid, benzenesulphonic acid, p-toluenesulphonic acid, p-chlorobenzenesulphonic acid, N,N-dimethylaminosulphonic acid, N,N-diethylaminosulphonic acid, N,N-bis(β-chloroethyl)aminosulphonic acid, N,N-diisobutylaminosulphonic acid, N,N-dibutylaminosulphonic acid, pyrrolidino-, piperidino-, piperazino-, N-methylpiperazino- and morpholinosulphonic acid.

The hydroxy group may be functionally modified, for example by etherification or esterification.

Suitable ether residues are the residues known to the skilled person. Preference is given to ether residues which can easily be eliminated, such as, for example, the tetrahydropyranyl, tetrahydrofuranyl, trimethylsilyl, tert-butyldimethylsilyl, tert-butyldiphenylsilyl or tribenzylsilyl radicals.

Suitable acyl radicals are the carboxylic acids mentioned under $R^7$. Examples of those which may be mentioned by name are acetyl, propionyl, butyryl and benzoyl.

Suitable for the salt formation are inorganic and organic bases as known to the skilled person for the formation of physiologically tolerated salts. Examples which may be mentioned are alkali metal hydroxides such as sodium and potassium hydroxides, alkaline earth metal hydroxides, such as calcium hydroxide, ammonia, amines such as ethanolamine, diethanolamine, triethanolamine, N-methylglucamine, morpholine, tris(hydroxymethyl)methylamine, etc.

Compounds of the general formula I which have proved to be particularly effective are those where
$R^1$ is a $CH_2OH$, $—COOR^2$, $—CONHR^2$ or $—CONHR^3$ group,
$R^2$ is a hydrogen or
a $C_1$-$C_{10}$-alkyl radical which is linear or branched, optionally mono- to polyunsaturated and is optionally monosubstituted by fluorine, chlorine or bromine, by $C_1$-$C_4$-alkoxy, substituted $C_3$-$C_{10}$-aryl or optionally substituted $C_3$-$C_{10}$-aroyl, di-$C_1$-$C_5$-alkylamino or tri-$C_1$-$C_5$-alkylamino, a $C_5$-$C_6$-cycloalkyl which is optionally substituted by $C_1$-$C_4$-alkyl,
a $C_3$-$C_{10}$-aryl radical which is optionally substituted by phenyl which may be substituted in position 3 or 4 by fluorine, chlorine, alkoxy or trifluoromethyl or in position 4 by hydroxy,
a $C_5$-$C_6$-heterocycloalkyl which may be interrupted one or more times by nitrogen, oxygen or sulphur,
$R^3$ is a $C_1$-$C_{10}$-carboxylic acid or $C_1$-$C_{10}$-sulphonic acid,
A is a cis-CH=CH— or —$CH_2$—$CH_2$— group,
B is a trans-CH=CH— or —$CH_2$—$CH_2$— group,
W is a $C_2$-$C_6$-alkylene,
$R^4$ is a hydroxy group,
$R^5$ is a hydrogen, a $C_1$-$C_6$-alkyl or $C_1$-$C_{10}$-alkenyl group and
n is the number 1-4, preferably 2-3.

Compounds of the general formula I which have proved to be very particularly effective are those where
$R^1$ is a —$CH_2OH$, —$COOR^2$—$CONHR^2$ or —$CONHR^3$ group,
$R^2$ is a hydrogen or a $C_1$-$C_4$-alkyl which is optionally substituted by phenyl,
a $C_5$-$C_6$-cycloalkyl,
a $C_3$-$C_6$-aryl which is optionally substituted by phenyl,
$R^3$ is a $C_1$-$C_6$-carboxylic acid or $C_1$-$C_6$-sulphonic acid,
A is a cis-CH=CH— or —$CH_2$—$CH_2$— group,
B is a trans-CH=CH— or —$CH_2$—$CH_2$— group,
W is a $C_2$-alkylene,
$R^4$ is a hydroxy group,
$R^5$ is a hydrogen, saturated $C_1$-$C_4$-alkyl or $C_1$-$C_5$-alkenyl, and
n is the number 1-4, preferably 2-3, more preferably 2.

In a presently preferred embodiment, the EP2 agonist useful in treating autoimmune diseases according to the present invention is the 9-chloro-15-deoxyprostaglandin derivative (5Z,13E)-(9R,11R)-9-chloro-11-hydroxy-17,17-tetramethylene-20-nor-5,13-prostadienoic acid.

The prostane derivatives of the above general formula I are prepared by the reaction of an aldehyde of the general formula II

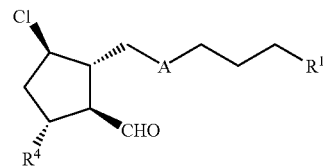

II (wherein $R^1$ has the meaning of the radicals —$COOR^2$, —$CONHR^3$, and A, and $R^4$ is as defined above, where the free OH group in $R^4$ is protected)
with the carbanion of the sulphone of the general formula III

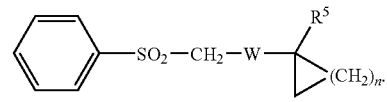

III

Acetylation of the resulting hydroxysulphone is followed by reductive elimination to give the olefin and, where appropriate, a subsequent deprotection of the hydroxy groups which are protected in any sequence and, where appropriate, esterification, etherification and/or hydrogenation of double bonds and/or esterification of an esterified carboxy group ($R^1$=COOR$^2$) and/or of a free carboxy group (COOR$^2$ with $R^2$=H) and/or conversion of a free carboxy group (COOR$^2$ with $R^2$=H) into an amide ($R^1$=CONR$^2$) and/or reduction of a free or esterified carboxy group ($R^1$=CONHR$^3$).

Reaction of the aldehyde of the general formula II with the carbanion generated from the sulphone III takes place in a manner known per se using an inert solvent such as, for example, tetrahydrofuran or diethyl ether at temperatures between −100° C. and 24° C., preferably −100° C. to −70° C. The carbanion of the sulphone III is generated in a conventional way with a base such as, for example, butyllithium, methyllithium, potassium tert-butoxide, sodium hydride, lithium diisopropylamide, preferably butyllithium. The carbanion formation is carried out at temperatures from −78° C. to 25° C., preferably at −78° C.

Acetylation of the generated hydroxy group takes place in a known manner with acetic anhydride, where appropriate in the presence of a base, for example pyridine, at temperatures between −78° C. and 25° C.

Reductive elimination of the intermediate acetoxy sulphone to give the trans-olefin of the general formula I takes place with magnesium powder in methanol with the addition of a catalytic amount of chlorotrimethylsilane. The reaction is carried out at temperatures between 0° C. and 60° C., preferably between 15° C. and 25° C. Alternatively, the reductive elimination can also be carried out with sodium amalgam.

Reduction to give the compounds of the general formula I with $R^1$ in the meaning of a —CH$_2$OH group is carried out with a reducing agent suitable for reducing esters or carboxylic acids, such as, for example, lithium aluminium hydride, diisobutylaluminium hydride etc. Suitable solvents are diethyl ether, tetrahydrofuran, dimethoxyethane, toluene etc. The reduction is carried out at temperatures from −30° C. to the boiling point of the solvent used, preferably 0° C. to 30° C.

Functionally modified hydroxy groups are liberated by known methods. For example, elimination of hydroxy protective groups such as, for example, the tetrahydropyranyl radical is carried out in an aqueous solution of an organic acid, such as, for example, oxalic acid, acetic acid, propionic acid, inter alia, or in an aqueous solution of an inorganic acid such as, for example, hydrochloric acid. It is expedient to add a water-miscible inert organic solvent to improve the solubility. Examples of suitable organic solvents are alcohols such as methanol and ethanol, and ethers such as dimethoxyethane, dioxane and tetrahydrofuran. Tetrahydrofuran is preferably used. The elimination is preferably carried out at temperatures between 20° C. and 80° C.

The acyl groups are hydrolysed for example with alkali metal or alkaline earth metal carbonates or hydroxides in an alcohol or in the aqueous solution of an alcohol. Suitable alcohols are aliphatic alcohols such as, for example, methanol, ethanol, butanol etc., preferably methanol. Alkali metal carbonates and hydroxides which may be mentioned are potassium and sodium salts. The potassium salts are preferred.

Examples of suitable alkaline earth carbonates and hydroxides are calcium carbonate, calcium hydroxide and barium carbonate. The reaction takes place at from −10° C. to +70° C., preferably at +25° C.

The ester group —COOR$^2$ for $R^1$, for example in which $R^2$ is an alkyl group having 1-10 C atoms, is introduced by the methods known to the skilled person. The 1-carboxy compounds are reacted for example with diazohydrocarbons in a manner known per se. Esterification with diazohydrocarbons takes place for example by mixing a solution of the diazohydrocarbon in an inert solvent, preferably in diethyl ether, with the 1-carboxy compound in the same or in a different inert solvent, such as, for example, methylene chloride. After the reaction is complete in 1 to 30 minutes, the solvent is removed and the ester is purified in a conventional way. Diazoalkanes are either known or can be prepared by known methods (Org. Reactions Vol. 8, pages 389-394 (1954)).

The ester group COOR$^2$ for $R^1$, in which $R^2$ is a substituted or unsubstituted aryl group, is introduced by the methods known to the skilled person. For example, the 1-carboxy compounds are reacted with the appropriate aryl hydroxy compounds with dicyclohexylcarbodiimide in the presence of a suitable base, for example pyridine, DMAP, triethylamine, in an inert solvent. Suitable solvents are methylene chloride, ethylene chloride, chloroform, ethyl acetate, tetrahydrofuran, preferably chloroform. The reaction is carried out at temperatures between −30° C. and +50° C., preferably at 10° C.

If it is intended to reduce C=C double bonds present in the initial product, the hydrogenation takes place by methods known per se.

Hydrogenation of the 5,6 double bond is carried out in a manner known per se at low temperatures, preferably at about −20° C., in a hydrogen atmosphere in the presence of a noble metal catalyst. An example of a suitable catalyst is 10% palladium on carbon.

If both the 5,6 double bond and the 13,14 double bond are hydrogenated, a higher temperature is used, preferably about 20° C.

The prostaglandin derivatives of the general formula I with $R^2$ meaning a hydrogen atom can be converted into a salt by neutralization using suitable amounts of the appropriate inorganic bases. For example, dissolving the appropriate prostaglandin acids in water containing the stoichiometric amount of the base results, after the water has been evaporated off or a water-miscible solvent, e.g. alcohol or acetone, has been added, in the solid organic salt.

An amine salt is prepared in a conventional way by dissolving the prostaglandin acid for example in a suitable solvent, for example ethanol, acetone, diethyl ether, acetonitrile or benzene, and adding at least the stoichiometric amount of the amine to this solution. This usually results in the salt in solid form, or it is isolated in the usual way after evaporation of the solvent.

The amide group —CONHR$^3$ for $R^1$ is introduced by methods known to the skilled person. The carboxylic acids of the general formula I ($R^2$=H) are initially converted into the mixed anhydride with isobutyl chloroformate in the presence of a tertiary amine such as, for example, triethylamine. Reaction of the mixed anhydride with the alkali metal salt of the appropriate amine or with ammonia ($R^3$=H) takes place in an inert solvent or solvent mixture, such as, for example, tetrahydrofuran, dimethoxyethane, dimethylformamide, hexamethylphosphoric triamide, at temperatures between −30° C. and +60° C., preferably at 0° C. to 30° C.

A further possibility for introducing the amide group —CONHR$^3$ for $R^1$ consists in reacting a 1-carboxylic acid of the general formula I ($R^2$=H), in which there is optionally intermediate protection of free hydroxy groups, with compounds of the general formula IV

$$O=C=N-R^3 \qquad\qquad IV$$

in which $R^3$ has the meaning indicated above.

Reaction of the compound of the general formula I ($R^2$=H) with an isocyanate of the general formula IV takes place where appropriate with addition of a tertiary amine such as, for example, triethylamine or pyridine. The reaction can be carried out without solvent or in an inert solvent, preferably acetonitrile, tetrahydrofuran, acetone, dimethylacetamide, methylene chloride, diethyl ether, toluene, at temperatures between −80° C. to 100° C., preferably at 0° C. to 30° C.

If the starting material comprises OH groups in the prostane residue, these OH groups are also reacted. If the final products eventually desired comprise free hydroxy groups in the prostane residue, it is expedient to start from starting materials with intermediate protection thereof by ether or acyl radicals which can preferably be easily eliminated.

The aldehydes of the general formula II which are used as starting material are known or can be prepared for example by selective epoxidation in a manner known per se of the 13,14 double bond of a 9-haloprostaglandin of the general formula V, preferably with $R^1$ meaning a —$COOCH_3$ group, with tert-butyl hydroperoxide and titanium(IV) isopropoxide in methylene chloride at −20° C.

Subsequent epoxide cleavage with periodic acid in diethyl ether and, where appropriate, protection of the 11-hydroxy group, for example with dihydropyran, affords the aldehyde of the general formula II.

The sulphone of the general formula III used as starting material can be prepared from cycloalkylcarboxylic acids of the general formula VII in which n has the meaning indicated above by alkylation with an alkyl halide of the general formula VIII in which $R^5$ has the meaning indicated above, and halogen can be iodine, chlorine or bromine.

Esterification of IX with methyl iodide and potassium carbonate in acetone is followed by reduction of the resulting methyl ester to the alcohol with lithium aluminium hydride in diethyl ether. Oxidation of the alcohol with $SO_2$-pyridine complex in the presence of triethylamine in a mixture of dimethyl sulphoxide and methylene chloride affords the aldehyde of the general formula X. Subsequent Wittig-Horner reaction and, where appropriate, hydrogenation of the double bond to give XI leads, after reduction with diisobutylaluminium hydride, to the alcohol of the general formula XII. Hydrogenation of the double bond can, however, also be carried out after reduction of the ester XI to the alcohol XII, with W meaning a double bond.

Subsequent replacement of the hydroxy group takes place after intermediate tosylation by reaction with thiophenol in toluene. The thioether XIII obtained in this way is finally oxidized in an aqueous methanolic solution to the sulphone of the general formula III.

In a further embodiment of the invention, the EP2 and EP4 agonists are selected from those reported by Ono Pharmaceuticals, by Merck and by Pfizer.

The pharmacologically active EP2 and EP4 agonists useful in the present invention can be processed in accordance with conventional methods of galenic pharmacy to produce medicinal agents for treating diseases associated with influenza A viruses, and particularly the H5N1 virus. The pharmaceutical compositions comprise the EP agonist in an effective amount (that is, an amount effective to treat an influenza A viral disease) and one or more pharmaceutically acceptable excipients.

Suitable excipients may include, but are not limited to, pharmaceutical, organic or inorganic inert carrier materials suitable for enteral, parenteral or topical administration which do not deleteriously react with the active compounds. Suitable pharmaceutically acceptable carriers include, but are not limited to, water, salt solutions, alcohols, gelatine, gum arabic, lactate, starch, magnesium stearate, talc, vegetable oils, polyalkylene glycols, polyvinyl pyrrolidone, hydroxylmethylcellulose, silicic acid, viscous paraffin, fatty acid monoglycerides and diglycerides, and the like. The pharmaceutical products may be in solid form, for example as tablets, coated tablets, suppositories or capsules, or in liquid form, for example as solutions, suspensions or emulsions. They may additionally comprise, where appropriate, auxiliary agents such as lubricants, preservatives, stabilizers, wetting agents, emulsifiers, salts to alter the osmotic pressure, buffers, coloring, flavoring, and/or aromatic substances and the like that do not deleteriously react with the active compounds. Examples of suitable pharmaceutical compositions include the following:

Aerosol solutions are expediently produced for delivery via inhalation.

Particularly suitable for oral use are tablets, coated tablets or capsules with talc and/or carbohydrate carriers or binders, such as, for example, lactose, maize starch or potato starch. Use is also possible in liquid form, such as, for example, as fluid to which a sweetener is added where appropriate.

Sterile, injectable, aqueous or oily solutions are used for parenteral administration, as well as suspensions, emulsions or implants, including suppositories. Ampoules are convenient unit dosages. Sustained release compositions can be formulated including those wherein the active compound is protected with differentially degradable coatings, e.g., by microencapsulation, multiple coatings, etc.

Carrier systems which can also be used are surface-active excipients such as salts of bile acids or animal or vegetable phospholipids, but also mixtures thereof, and liposomes or constituents thereof. Transdermal patches may also be used as delivery means.

The dosage of the EP2 and/or EP4 therapeutic agent(s) will be that amount that is effective to treat an influenza A viral disease. The effective amount of active ingredient may vary depending on the route of administration, the age and weight of the patient, the nature and severity of the disorder to be treated, and similar factors. The effective amount can be determined by methods known to those of skill in the art. The daily dose is generally about 0.1-200 μg/kg/day, preferably about 0.5-10 μg/kg/day, when administered to human patients, it being possible for the dose to be given as a single dose to be administered once or divided into two or more daily doses.

The EP2 and/or EP4 agonists may be delivered as a co-treatment together with other anti-viral or anti-inflammatory compounds, such as, but not limited to, oseltamivir (Tamiflu™) and zanamivir (Relenza™). The compounds may be delivered to the patient at the same time or sequentially as separate formulations, or they may be combined and delivered as a single formulation.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

EXAMPLES

Example 1

Demonstration of Nileprost Inhibition of T Lymphocyte Th-1 Cytokine Release

Principle:

The activation of a human T lymphocyte by an antigen-presenting cell and antigen through the T cell receptor is mimicked in experimental conditions by the lectin Concanavilin A (ConA). It is known that ConA binds to the T cell receptor and stimulates the cell to release various cytokines. The binding of Nileprost to the EP receptor inhibits various cytokine release. One of the Th-1 released cytokines is IFN-γ. The biochemistry and biological activities of IFN-γ have been extensively reviewed in the literature.

Detection Method:

Human IFN-γ is a dimer of the expressed 143 amino acid protein. Enzyme-linked immunosorbant assays (ELISA) based on antibodies specific to IFN-γ are commercially available. Standards and samples are pipetted into the wells of a microplate. An antibody specific to human IFN-γ is added to the wells. A substrate is added to the wells and color develops in proportion to the amount of IFN-γ bound. The intensity of the color is measured.

Procedure:

Peripheral blood lymphocytes were isolated from human donors using a Ficoll density gradient and residual erythrocytes were removed by selective lysis. The lymphocytes are cultured at approximately $10^6$ cells per mL in RPMI1640 with 10% additional fetal bovine serum. The cell cultures were activated with 2 μg/ml of ConA as described above. Nileprost was added at various dilutions during the ConA activation. Cells were incubated for approximately 18 hr at 37° C. IFN-γ released during activation was measured by ELISA.

Nileprost Inhibition (percent)
human T cells
ConA stimulation
Percent inhibition of IFN-γ compared to uninhibited control

| Nileprost (nM) | 0 | 0.5 | 1.25 | 2.5 | 5 | 10 | 20 |
|---|---|---|---|---|---|---|---|
| Donor 1 | 0% | 17% | 23% | 45% | 56% | 50% | 67% |
| std. deviation | 21% | 21% | 3% | 11% | 10% | 10% | 5% |
| Donor 2 | 0% | 2% | 11% | 17% | 35% | 43% | 41% |
| std. deviation | 17% | 29% | 21% | 19% | 6% | 10% | 7% |
| Donor 3 | 0% | 26% | 36% | 43% | 54% | 64% | 68% |
| std. deviation | 12% | 9% | 2% | 3% | 2% | 7% | 10% |
| Donor 4 | 0% | 21% | 29% | 31% | 48% | 55% | 56% |
| std. deviation | 13% | 6% | 12% | 8% | 8% | 5% | 6% |

| Nileprost (nM) | 0 | 0.04 | 0.11 | 1 | 3 | 9 | 83 | 250 |
|---|---|---|---|---|---|---|---|---|
| Donor 5 | 0% | 16% | 22% | 43% | 56% | 59% | 57% | 59% |
| Std. deviation | 6% | 0% | 9% | 3% | 1% | 9% | 3% | 0% |
| Donor 6 | 0% | 7% | 16% | 32% | 46% | 60% | 60% | 76% |
| Std. deviation | 6% | 20% | 19% | 13% | 14% | 10% | 4% | 1% |
| Donor 7 | 0% | 9% | 22% | 24% | 22% | 48% | 65% | 57% |
| Std. deviation | 11% | 6% | 11% | 11% | 5% | 8% | 3% | 15% |
| Donor 8 | 0% | 27% | 34% | 51% | 71% | 73% | 85% | 83% |
| Std. deviation | 15% | 10% | 6% | 2% | 3% | 5% | 5% | 4% |

Nileprost showed, dose responsively, very high inhibitory activity in the T lymphocyte Th-1 cytokine release.

Example 2

Demonstration of Nileprost Inhibition of Proinflammatory Cytokine Release

Principle:

The activation of a human T lymphocyte by an antigen-presenting cell and antigen through the T cell receptor is mimicked in experimental conditions by the lectin Concanavilin A (ConA). It is known that ConA binds to the T cell receptor and stimulates the cell to release various cytokines. The binding of Nileprost to the EP receptor inhibits various cytokine release. One of the pro-inflammatory cytokines inhibited is TNFα. The biochemistry and biological activities of TNFα have been extensively reviewed in the literature.

Detection Method:

Human TNFα is a trimer of the expressed protein. Enzyme-linked immunosorbant assays (ELISA) based on antibodies specific to TNFα are commercially available. Standards and samples are pipetted into the wells of a microplate. An antibody specific to human TNFα is added to the wells. A substrate is added to the wells and color develops in proportion to the amount of TNFα bound. The intensity of the color is measured.

Procedure:

Peripheral blood lymphocytes were isolated from human donors using a Ficoll density gradient and residual erythrocytes were removed by selective lysis. The lymphocytes are cultured at approximately $10^6$ cells per mL in RPMI 1640 with 10% additional fetal bovine serum. The cell cultures were activated with 2 μg/ml of ConA as described above. Nileprost was added at various dilutions during the ConA activation. Cells were incubated for approximately 18 hr at 37° C. TNFα released during activation was measured by ELISA.

| Nileprost Inhibition (percent) human T cells ConA stimulation Percent inhibition of TNFα compared to uninhibited control | | | | | | | |
|---|---|---|---|---|---|---|---|
| Nileprost (nM) | 0 | 0.5 | 1.25 | 2.5 | 5 | 10 | 20 |
| Donor 1 | 0% | 7% | 14% | 24% | 47% | 46% | 50% |
| Std. deviation | 21% | 15% | 4% | 17% | 14% | 9% | 22% |
| Donor 2 | 0% | 1% | 5% | 19% | 36% | 49% | 46% |
| Std. deviation | 2% | 15% | 15% | 5% | 4% | 9% | 5% |
| Nileprost (nM) | 0 | 0.04 | 0.11 | 1 | 3 | 9 | 83 | 250 |
| Donor 3 | 0% | 1% | 4% | 24% | 28% | 53% | 61% | 49% |
| Std. deviation | 21% | 22% | 32% | 13% | 4% | 4% | 15% | 30% |
| Donor 4 | 0% | 11% | 16% | 37% | 48% | 67% | 76% | 76% |
| Std. deviation | 17% | 2% | 14% | 9% | 5% | 5% | 3% | 6% |

Example 3

Demonstration of Nileprost Inhibition of Cytotoxic CD8+ Lymphocyte Cytokine Release Principle:

The activation of a human T lymphocyte by an antigen-presenting cell and antigen through the T cell receptor is mimicked in experimental conditions by the addition of antibodies to the CD3 subunit of the T cell receptor and antibodies to the CD28 costimulatory receptor. It is known that anti-CD3 anti-CD28 binding to T lymphocytes stimulates the cells to release various cytokines. Some of these cytokines are IL-2, IFN-γ and GM-CSF. The biochemistry and biological activities of these cytokines have been extensively reviewed in the literature. The binding of Nileprost to the EP receptor inhibits the release of various CD8+ cytokines.

Detection Method:

Multi-cytokine immunosorbant assays based on antibodies specific to human cytokines are commercially available. Standards and samples are pipetted into sample tubes. A monoclonal antibody specific for a cytokine is covalently linked to a fluorescent bead set, which captures the cytokine. A complementary biotinylated monoclonal cytokine antibody then completes the immunological sandwich and the reaction is detected with streptavidin-phycoerythrin.

Procedure:

CD14-negative populations were isolated from four donors by Miltenyi CD14 beads. The four populations were allowed to rest at $5 \times 10^6$/mL in separate flasks overnight in RPMI 1640, 10% fetal bovine serum. Meanwhile, anti-CD3 antibody (OKT3, functional antibody, eBioscience) were bound to 10 cm plates at 5 μg/mL in sodium carbonate binding buffer at 4° C. The next day, the cells were mixed and 1×09 cells were taken for CD8 isolation using the Milenyi CD8 isolation kit (negative selection). The resulting $3.9 \times 10^8$ CD8 cells were resuspended in medium at $4 \times 10^6$/mL and added to the 10 cm CD3-bound plates. Soluble anti-CD28 (2-5 μg/mL) and 1 μM Nileprost or vehicle alone were added to the CD8 cells. Incubation was continued overnight and cytokines were detected as described above. The results are presented below.

| Nileprost Inhibition (percent) | | |
|---|---|---|
| | Nileprost | standard deviation |
| human CD8 cells Anti-CD3/CD28 stimulation Percent inhibition of IFN-γ compared to uninhibited control | | |
| Donor 1 | 79% | 1% |
| Donor 2 | 59% | 1% |
| Donor 3 | 79% | 2% |
| Donor 4 | 80% | 1% |
| human CD8 cells Anti-CD3/CD28 stimulation Percent inhibition of GM-CSF compared to uninhibited control | | |
| Donor 1 | 77% | 0% |
| Donor 2 | 65% | 2% |
| Donor 3 | 87% | 1% |
| Donor 4 | 61% | 6% |
| human CD8 cells Anti-CD3/CD28 stimulation Percent inhibition of IL-2 compared to uninhibited control | | |
| Donor 1 | 71% | 0% |
| Donor 2 | 68% | 4% |
| Donor 3 | 88% | 0% |
| Donor 4 | 70% | 5% |

Nileprost showed very high inhibitory activity in the cytotoxic CD8+ lymphocyte cytokine release.

Example 4

Demonstration of Nileprost Inhibition of Human Monocyte-Derived Dendritic Cell (DC) Cytokine Release Principle:

Dendritic cells (DCs) are the most potent antigen-presenting cells and play a central role in immune response. Following stimulation through the toll-like receptors TLR, DCs express and release proinflammatory cytokines and chemokines and may induce activation and proliferation of naïve T cells. The binding of Nileprost to the EP receptor inhibits TLR4 ligand (LPS)-stimulated IL-12 release. Therefore, Nileprost skews the CD4 T cell differentiation to a Th-2 lineage.

Detection Method:

IL-12 is a 75 kDa glycoprotein heterodimer (p70) composed of two genetically unrelated subunits linked by a disulfide bond. Enzyme-linked immunosorbant assays based on antibodies specific to IL-12 p70 are commercially available. Standards and samples are pipetted into the wells of a microplate. An antibody specific to human IL-12 is added to the wells. A substrate is added to the wells and color develops in proportion to the amount of IL-12 bound. The intensity of the color is measured.

Procedure:

Human monocyte-derived dendritic cells were isolated from human donors using a Ficoll density gradient and residual erythrocytes were removed by selective lysis. CD14 MicroBeads were used for separation of human cells based on the expression of the CD14 antigen. The dendritic cells were cultured at approximately $1.5 \times 10^6$ cells per mL in RPMI1640 with fetal bovine serum, 200 ng/mL GM-CSF (Leukine) and 10 ng/mL IL-4. The cells grew for a period of 3 days and then the media was changed. 10 ng/mL LPS was used to activate the cells. 1 µM of Nileprost and 1 µM of $PGE_2$ were added during the LPS stimulation. Cells were incubated for approximately 18 hr at 37° C. IL-12 released during activation was measured by ELISA. The results are presented below.

| Nileprost Inhibition (percent) Human monocyte-derived dendritic cells LPS stimulation Percent inhibition of IL-12 compared to uninhibited control | | |
|---|---|---|
| | Nileprost | PGE2 |
| Donor 1 | 84% | 80% |
| Donor 2 | 51% | 33% |
| Donor 3 | 69% | 83% |
| Donor 4 | 66% | 72% |

Nileprost showed very high inhibitory activity in human monocyte-derived dendritic cell (DC) cytokine release.

Example 5

Human donor monocyte-derived dendritic cells were cultured in RPMI-1640 containing 10% fetal bovine serum for six days in the presence of 10 ng/mL IL4 and 200 ng/mL GM-CSF. The cells were activated with various activation stimuli: 10 ng/mL LPS (Sigma), 5 µg/mL Recombinant human CD-40 ligand (R&D Systems), or 5 µM Human CpG-DNA (HyCult Biotechnology) in the presence of prostaglandin E2 ($PGE_2$) (1 µM), vehicle control (DMSO) or test substances (1 µM) for 18 hours. The levels of cell culture supernatant TNFα for individual donors was measured by commercial ELISA kits. The test substances [results with (5Z,13E)-(9R,11R)-9-chloro-[1-hydroxy-17,17-tetramethylene-20-nor-5,13-prostadienoic acid (Test Substance 1) and another EP agonist (Test Substance 2) are shown in the Table below] led to an inhibition in the cytokine levels measured in the culture supernatant as shown in the Table below.

| Inhibition of TNFα Release from activated monocytic cells | | |
|---|---|---|
| Test Substance + LPS | Donor 4 (TNFα pg/ml) | Donor 6 (TNFα pg/ml) |
| Vehicle | 3566.9 | 10750.1 |
| PGE2 | 0.0 | 174.8 |
| Test Substance 1 | 643.6 | 753.7 |
| Test Substance 2 | 179.4 | 676.1 |

| Test Substance + CD40 ligand | Donor 3 (TNFα pg/ml) | Donor 4 (TNFα pg/ml) | Donor 6 (TNFα pg/ml) |
|---|---|---|---|
| Vehicle | 567.1 | 546.3 | 541.8 |
| PGE2 | 147.9 | 87.0 | 54.2 |
| Test Substance 1 | 274.3 | 226.8 | 142.4 |
| Test Substance 2 | 209.4 | 211.2 | 84.4 |

| Inhibition of TNFα Release from activated monocytic cells | | |
|---|---|---|
| Test Substance + CpG | Donor 1 (TNFα pg/ml) | Donor 3 (TNFα pg/ml) | Donor 6 (TNFα pg/ml) |
| Vehicle | 2155.9 | 1340.7 | 467.8 |
| PGE2 | 104.5 | 70.0 | 106.2 |
| Test Substance 1 | 291.3 | 599.4 | 115.9 |
| Test Substance 2 | 546.9 | 74.8 | 84.8 |

Example 6

Demonstration of Nileprost Inhibition of TNFα Release from Viral RNA-Activated Human Monocyte-Derived Dendritic Cells The test substance (Nileprost) was used to inhibit the release of TNFα from synthetic viral RNA-activated human monocyte-derived dendritic cells. Cells were cultured in vitro as described in Example 4 and Example 5. Cells were activated with 2 µg/mL Poly(I:C), a synthetic derivative of double-strand RNA (a component of the influenza A virus) in the presence or absence of one micromolar test substance and cultured for 18 hours. The levels of cell culture supernatant TNFα were measured by commercial ELISA kits. The test substance (Nileprost) caused a significant decrease in Poly(I:C)-induced TNFα.

| Poly IC-stimulated monocyte-derived dendritic cells TNFα percent inhibition from untreated control | | | | |
|---|---|---|---|---|
| | Donor 1 | Donor 2 | Donor 3 | Donor 4 |
| PGE2 | 96% | 63% | 81% | 29% |
| Nileprost | 89% | 45% | 74% | 36% |
| Vehicle | 0% | 0% | 0% | 0% |

Example 7

Demonstration of Beraprost Inhibition of TNFα Release from Viral RNA-Activated Human Peripheral Blood Lymphocytes Following the procedures in Example 6, peripheral blood lymphocytes were isolated and cultured, after which they were activated with Poly(I:C) and further cultured. The levels of cell culture supernatant TNFα was then measured by ELISA kits. The test substance (Beraprost) caused a significant decrease in Poly(I:C)-induced TNFα, as shown in the Table below.

| Poly IC-stimulated peripheral blood lymphocytes TNFα percent inhibition from untreated control | | | | | | | | |
|---|---|---|---|---|---|---|---|---|
| Beraprost (nM) | 0 | 0.04 | 0.11 | 1 | 3 | 9 | 83 | 250 |
| Donor 1 | 0% | 19% | 19% | 11% | 36% | 46% | 56% | 67% |
| Standard deviation | 19% | 10% | 10% | 2% | 4% | 14% | 15% | 0% |
| Donor 2 | 0% | 4% | 26% | 28% | 11% | 35% | 56% | 59% |
| Standard deviation | 23% | 36% | 18% | 10% | 32% | 31% | 16% | 5% |

Example 8

Tolerance in Humans after Oral Administration of Nileprost

Study A. Tolerance and Pharmacokinetics 14 volunteers were given a single oral dose of Nileprost at 2, 4, 8, 16, 32, or 65 μg. The following parameters were studied: Blood pressure, heart rate, clinical chemistry, platelet aggregation, and ECG.

No findings but enteropooling in higher doses, indicating good tolerance to Nileprost.

| Pharmacokinetics: mean $c_{max}$ after | | |
|---|---|---|
| 32 μg: | 840 ± 30 pg/mL | 2.1 nM |
| 65 μg: | 929 ± 254 pg/mL | 2.3 nM |

Study B. Single Administration up to 375 μg 12 volunteers were given a single oral dose of Nileprost at 50, 75, 112, 255 or 375 μg. The following parameters were studied: Blood pressure, heart rate, ECG, lung function, clinical chemistry and hematology, platelet aggregation, and stools.

No findings but "painless diarrhea" in higher doses (255 μg and 375 μg), indicating tolerance to Nileprost.

| Pharmacokinetics: mean $c_{max}$ after | | |
|---|---|---|
| 50 μg: | 566 pg/mL | 1.4 nM |
| 75 μg: | 869 pg/mL | 2.2 nM |
| 112 μg: | 803 pg/mL | 2.0 nM |
| 170 μg: | 954 pg/mL | 2.4 nM |
| 255 μg: | 1709 pg/mL | 4.3 nM |
| 375 μg: | 1716 pg/mL | 4.3 nM |

What is claimed is:

1. A method of treating an influenza A virus infection in a patient in need of such treatment, the method comprising administering to the patient an effective amount of a therapeutic agent selected from the group consisting of nileprost and beraprost.

2. The method of claim 1, wherein said therapeutic agent is beraprost.

3. The method of claim 1, wherein said therapeutic agent is nileprost.

4. The method of claim 1, wherein the influenza A virus is H5N1 or a mutation thereof.

5. The method of claim 2, wherein the influenza A virus is H5N1 or a mutation thereof.

6. The method of claim 3, wherein the influenza A virus is H5N1 or a mutation thereof.

7. The method according to any one of claim 1, 2, 3, 5, or 6, wherein said therapeutic agent inhibits the release of inflammatory cytokines and/or chemokines in human alveolar and bronchial epithelial cells.

8. The method of claim 2, wherein said therapeutic agent inhibits the release of inflammatory cytokines and/or chemokines in human alveolar and bronchial epithelial cells.

9. The method of claim 3, wherein said therapeutic agent inhibits the release of inflammatory cytokines and/or chemokines in human alveolar and bronchial epithelial cells.

10. The method of claim 4, wherein said therapeutic agent inhibits the release of inflammatory cytokines and/or chemokines in human alveolar and bronchial epithelial cells.

11. The method of claim 5, wherein said therapeutic agent inhibits the release of inflammatory cytokines and/or chemokines in human alveolar and bronchial epithelial cells.

12. The method of claim 6, wherein said therapeutic agent inhibits the release of inflammatory cytokines and/or chemokines in human alveolar and bronchial epithelial cells.

13. The method of claim 1, wherein said therapeutic agent inhibits the release of inflammatory cytokines and/or chemokines in peripheral blood lymphocytes.

14. The method of claim 2, wherein said therapeutic agent inhibits the release of inflammatory cytokines and/or chemokines in peripheral blood lymphocytes.

15. The method of claim 3, wherein said therapeutic agent inhibits the release of inflammatory cytokines and/or chemokines in peripheral blood lymphocytes.

16. The method of claim 4, wherein said therapeutic agent inhibits the release of inflammatory cytokines and/or chemokines in peripheral blood lymphocytes.

17. The method of claim 5, wherein said therapeutic agent inhibits the release of inflammatory cytokines and/or chemokines in peripheral blood lymphocytes.

18. The method of claim 6, wherein said therapeutic agent inhibits the release of inflammatory cytokines and/or chemokines in peripheral blood lymphocytes.

* * * * *